United States Patent [19]

Danby et al.

[11] 4,421,506
[45] Dec. 20, 1983

[54] FLOW-REGULATING ENTERIC FEEDING PUMP

[75] Inventors: Hal C. Danby, Palo Alto; Carl Ritson, San Jose, both of Calif.

[73] Assignee: Anatros Corporation, San Jose, Calif.

[21] Appl. No.: 338,012

[22] Filed: Jan. 8, 1982

[51] Int. Cl.³ .......................... A61M 5/00; F04B 43/08
[52] U.S. Cl. ...................................... 604/34; 604/250; 417/474
[58] Field of Search ............... 128/213, 214 R, 214 F, 128/DIG. 12; 417/474, 475, 478, 479

[56] References Cited

U.S. PATENT DOCUMENTS

| | | | |
|---|---|---|---|
| 3,778,195 | 12/1973 | Bamberg | 417/474 |
| 4,013,074 | 3/1977 | Siposs | 128/214 F X |
| 4,042,153 | 8/1977 | Callahan et al. | 128/214 F X |
| 4,273,121 | 6/1981 | Jassanalla | 417/474 X |
| 4,303,376 | 12/1981 | Siekmann | 417/474 X |

*Primary Examiner*—Stephen C. Pellergrino

*Attorney, Agent, or Firm*—C. Michael Zimmerman

[57] ABSTRACT

The pump is designed to dispense fluid nutrient at a selectable constant rate from a disposable, flexible plastic bag having a flexible enteric feeder tube attached to it. The bag is suspended from the pump frame with the outlet of the bag and the enteric feeder tube lowermost. The lower portion of the bag adjacent the outlet is then enclosed between a compliant rubber block on the frame, and a planar pressure plate mounted on a door hinged to the frame. The surfaces of the rubber block is provided with spaced, vertically extending protuberant ridges which, under the influence of the compressive force of the pressure plate, occlude the bag in the region about the outlet to define an effluent flow channel. Similarly, spaced horizontal ridges on the block define, within the flow channel, an unoccluded region which is isolted from the outlet by the lower horizontal ridge, and from the remaining volume of the bag, by the upper horizontal ridge.

23 Claims, 6 Drawing Figures

FLOW-REGULATING ENTERIC FEEDING PUMP

BACKGROUND OF THE INVENTION

This invention belongs generally to the field of apparatuses for the transport of fluids at controlled flow rates. More particularly, the invention pertains to flow-regulating pumps adapted to the handling of fluids which must be isolated from the surrounding environment either because the fluids are hazardous, or because contamination must be strictly avoided. Specifically, the invention is embodied in an apparatus for continuously administering fluid nutrients or medicaments internally to the human body, especially for the purpose of enteric feeding.

In medicine, the management of a variety of disorders or disabilities may at some point indicate the employment of enteric feeding. A common technique utilizes a nasogastric tube introduced through a nostril of the patient and extending from there into the stomach. Through this tube, a variety of easily digested fluid nutrients can be more-or-less continuously introduced into the stomach without requiring intervention by the patient, and without stress to the gastroenteric system of the patient. Consequently, the technique may often be employed for severely debilitated or comatose patients.

Because such patients are virtually unable to cope with malfunctions in the enteric feeding apparatus, and because constant supervision of the apparatus by a medical attendant is prohibitively expensive, a very high degree of reliability of the apparatus is essential if accidents are to be avoided. Moreover, the apparatus needs to be designed in such a way as to minimize daily expenses incurred through its use, since the period of time during which it is required may extend for months or even years. Finally, the apparatus must be as simple to use as possible, especially since attendants of very limited training may be required to use it, as when a patient is discharged from a medical or nursing facility to return home while continuing enteric feeding.

Chief among the malfunctions which must be avoided in an enteric feeding apparatus is the occurrence of a sudden inrush of the fluid nutrient, which could result in the filling of the esophagus, followed by the disastrous incursion of the fluid into the tracheo-pulmonary system. The consequences of such an inrush, such as pneumonia or suffocation, are obviously so serious that only exceptionally reliable, fail-safe designs can be considered.

Beyond the prevention of such a disastrous accident, the design of an enteric feeding apparatus should favor rapid and simple initial setup of the apparatus, and ease in changing the container bag. The flow rate of the fluid nutrient should be easy to establish and control, and long-term variations in the flow rate should not exceed ±15% without operator intervention.

DESCRIPTION OF THE PRIOR ART

The principal means of controlling the flow rate of enteric nutrient in the prior art were peristaltic pumps. Such pumps, which transport the nutrient through the enteric feeder tube by a process which imitates intestinal peristalsis, employ the principal of forcing the nutrient through the tube by producing a continuously moving occlusion travelling along some portion of the enteric tube.

In practice, the effect may be produced by mounting a number of occluding rollers on the periphery of a pump rotor, and by compressing a portion of the enteric feeder tube between these rollers and an arcuate pump housing member which is concentric with the pump rotor but spaced therefrom to accomodate the enteric tube. As the pump rotor revolves, the portion of enteric tube within the pump housing experiences a succession of occlusions travelling along its length as each successive roller presses into the tube and moves along it. Similar peristaltic pumps operate by drawing a short section of tubing around the periphery of a triangular rotor. As the pump revolves, the corners of the rotor press into the tube and create regions of occlusion traveling along the tube.

Characteristic of such peristaltic pumps is the ability to generate very considerable pressure if the pump outlet line should become constricted due to some mishap. This trait requires that their employment in biomedical or hazardous-fluid transport applications be handled very circumspectly, with adequate safeguards to control fluid pressure.

While peristaltic pump designs are simple in conception, their practical realization involves considerable precision, resulting in excessive cost and several other drawbacks as well. In particular, the section of the enteric tube which passes through the pump housing and thus becomes an integral part of the pumping process must at the present time be made of a relatively expensive silastic material such as silicone rubber.

Although cheaper materials such as polyethylene or PVC may be used in forming the remainder of the enteric tube, they have not proven satisfactory when their use was extended into the pumping region. This is true principally because they are not sufficiently elastic, and exhibit deformation by creep when subjected to the stresses necessary to occlude them. The result has been that the initial flow rate could not be maintained for more than a few minutes, after which it declined as the section of tube within the pumping region became inelastically flattened, reducing the volume of fluid delivered at each pass of the rollers.

Even when silicone rubber tubing is used in the pumping region, the tubing diameter has to be maintained to an uncommon degree of dimensional precision if anticipated flow rates are to be attained. This requirement of unusual dimensional precision applies especially to the inside diameter of the silicone rubber tube, since this dimension determines the fluid volume contained per unit length of the tube. However, the outside diameter must also be maintained within fairly tight tolerances, since variations here are certain to affect the forces on the rollers and may cause consequent variations in the speed of the pump rotor. Similarly, the hardness and resiliency of the rubber will also affect the forces required to occlude it, and may also vary the pumping speed. Consequently, the durometer specification of the rubber tube must be carefully maintained. The effect of these requirements has been that the cost of the disposable part of the peristaltic pump apparatus, including the enteric tube incorporating a section of silicone rubber, was simply too high.

In addition to excessive cost, the prior art peristaltic pumps are prone to become covered with a gummy residue of leaked or spilled enteric fluid. Since the pump is located below the container bag, any such leaks cause drops of fluid nutrient to run down the enteric tube and into the pump housing, causing an unsightly mess and occasionally also causing a malfunction of the pump mechanism.

SUMMARY OF THE INVENTION

The principal object of the present invention is the provision of a flow-regulating pump for use in an apparatus for administering fluid internally to the human body, particularly for the purpose of enteric feeding;

A second object of the present invention is the provision of such a pump having reduced running costs in comparison with known pumps;

A third object of the present invention is the provision of such a pump in a form which minimizes the likelihood of malfunction and substantially prevents the occurrence of a sudden inrush of fluid into the patient;

A fourth object of the present invention is the provision of such a pump in a form which is simple and convenient in use, such that it may be used by relatively untrained attendants;

A fifth object of the present invention is the provision of such a pump with means to secure a preselected constant flow rate.

In satisfying the above objects, the pump according to the present invention has a frame which includes means to secure a disposable flexible container bag of the fluid to be dispensed. The bag is supported in a generally vertical position with its outlet and enteric tube lowermost, and the lower region of the bag is then enclosed between a compliant rubber block on the frame and a planar pressure plate on a door hinged to the frame. The rubber block has on its face an array of protuberant ridges which are pressed against the bag as the door is closed to define a corresponding array of occluded regions, including a pair of spaced occluded regions extending vertically from the outlet port for a short distance within the bag to define an effluent flow channel, and a pair of spaced horizontal occluded regions extending across the flow channel to define between them an unoccluded pumping region within the flow channel.

An electromechanical system is provided to alternately draw the upper and lower ridges away from the bag, permitting controlled flow first into and then out of the unoccluded pumping region. A pump plunger is activated to expel fluid contained within the pumping region into the outlet port, and a shallow depression in the face of the rubber block defines the volume of fluid which can flow into the pumping region each time the upper horizontal ridge is withdrawn.

The electromechanical system may provide that the lower ridge is never fully mechanically withdrawn from occlusive compression of the bag, but is merely held in light occlusive contact therewith during the evacuation of the pumping region, such that the plunger always works against a constant pressure head at the outlet, improving the constancy of flow rate.

The above and other features, objects and advantages of the present invention, together with the best mode contemplated by the inventors for carrying out their invention will become more apparent upon reading the following detailed description of a preferred embodiment of the invention and perusing the associated drawing, in which the figures represent:

DETAILED DESCRIPTION OF A PREFERRED EMBODIMENT

Figure 1:
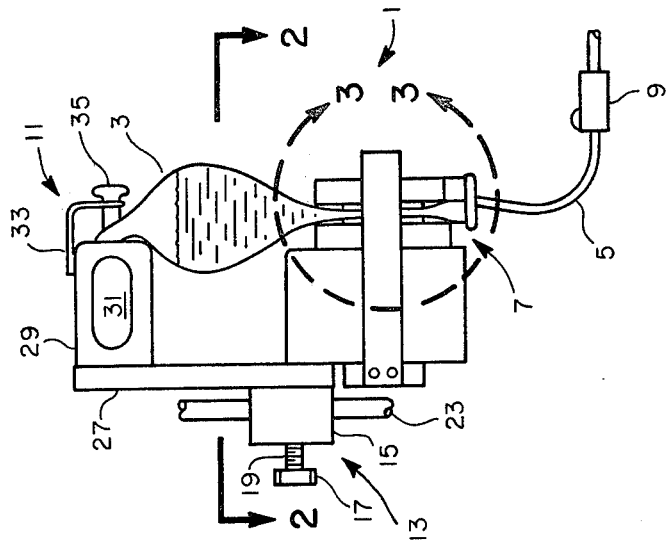
FIG. 1 is a side view of the enteric feeder apparatus according to the present invention.

In FIG. 1, an apparatus designed generally for dispensing fluid at a controlled rate from a flexible container bag is shown. The apparatus is more particularly a flow-regulating pump 1 for administering a fluid internally to the human body, especially for the controlled enteric feeding of a patient with an easily digested fluid nutrient by a method which includes introducing a nasogastric tube (not shown) into a nostril of the patient, and from there into the stomach. Accordingly, a flexible bag 3 containing the fluid nutrient is provided with an enteric feeder tube 5 extending from the lower edge of bag 3, to which it may be integrally joined, or merely removably connected in a fluid-tight fashion by any of several known connectors, the juncture being indicated generally by 7. The point of juncture of tube 5 and bag 3 forms an outlet port of bag 3, through which fluid effluent from the bag passes to travel along tube 5 to a shutoff clamp 9, and from there to the patient (not shown).

Reduced to its simplest and broadest terms, the functions of pump 1 are to support bag 3 in a vertical orientation with its outlet port lowermost, and to control the flow of fluid nutrient from bag 3 into tube 5 with some precision and considerable reliability. In particular, the occurrence of an uncontrolled high flow rate, or inrush, of fluid must be most strenuously guarded against in the design of such a pump, as mentioned earlier in this application.

These functions are achieved by a support clamp 11 which securely fastens the top of bag 3, and by a somewhat complex pump-bag interface region, enclosed within arrows 3—3, which forms the lower region of the bag into an integral, functioning part of the pump mechanism in a way which will be explained later in regard in FIGS. 3-6.

Pump 1 is provided with a mounting clamp 13 which includes a clamp body 15, a hand knob 17, a clamping screw 19 which is rotated by knob 17, and a clamping dog 21 which engages the threads of screw 19 and travels therealong when screw 19 is rotated. A tubular column 23 can thus be firmly engaged between dog 21 and a vee-shaped recess 25 on body 15, such that pump 1 can be securely but adjustably supported at a convenient height on column 23.

A pump spine 27 is fastened directly to clamp body 15, for example by screws, and serves as the main structural member uniting the other parts of pump 1. An upper support 29 joins spine 27 at the upper end thereof and serves principally as a locating member for the upper end of bag 3. However, by virtue of an oval opening 31 through support 29, a convenient carrying handle for transporting pump 1 is provided.

In the illustrated, prototypical embodiment, a clamp spring 33 has one end fastened to support 29, while its other end is transfixed by a clamping stud 35, one end of which serves to clamp bag 3 to support 29, while the other is conveniently enlarged to provide a finger grip. The portion of support 29 against which stud 35 presses bag 3 may preferably be provided with a shallow cylindrical recess (not shown) into which stud 35 presses a portion of the bag in order to more securely grip bag 3. In a production version, support clamp 11 might be considerably simplified by providing that bag 3 have an aperture defined within the sealed region of bag 3 near the top, such that a simple hook or peg could support the bag in the same way as described above.

Figure 2:
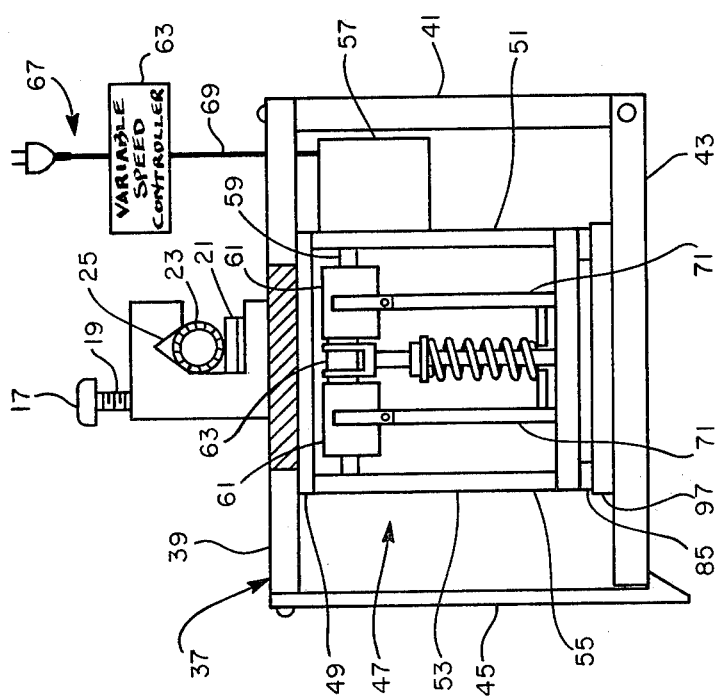
FIG. 2 is a top view of the apparatus of FIG. 1, shown partially in elevation and partially in section as viewed along lines 2—2 in FIG. 1.

To the lower end of spine 27 is fastened a pump housing 37 containing the major functioning parts of pump 1 which are responsible for its novel and improved ability to successfully produce and control a constant, preselected flow rate of fluid from bag 3 through tube 5. As best shown in FIG. 2, housing 37 includes a rectangular outer frame, the components of which are a back beam 39, a side beam 41 joined to back beam 39, a pump door 43 hinged at one edge to side beam 41, and a cantilevered door latch 45 which is joined to back beam 39, whence it extends to latch the free edge of door 43.

Housing 37 also includes a pump sub-frame 47 which is similarly formed as an open frame, having a back plate 49 joined to both spine 27 and back beam 39, and a pair of side plates 51 and 53 joined to both back plate 49 and to a front plate 55.

A pump motor 57, for example a stepper motor having a variable shaft speed of 1-15 rpm, is mounted on side plate 51, and drives a shaft 59 having a pair of large eccentric cams 61 flanking a small eccentric cam 63 at a speed which is established by a variable speed controller 65. Controller 65 may derive power from a convenient a.c. or d.c. source, such as from available electric mains by means of an ordinary flexible power cord 67, and deliver suitable controlled energization to motor 57 by means of a lead 69.

Lead 69 may also, in a closed-loop servo system, incorporate conductors carrying feedback signals for more accurate control of the flow rate of fluid from pump 1. For example, any of a variety of known transducers could be employed to derive a control signal which is an analog of motor speed, or even of fluid flow rate, and the energization of motor 57 could be adjusted in response to the variations of this control signal from a reference signal in a manner that is well known.

Figure 4:
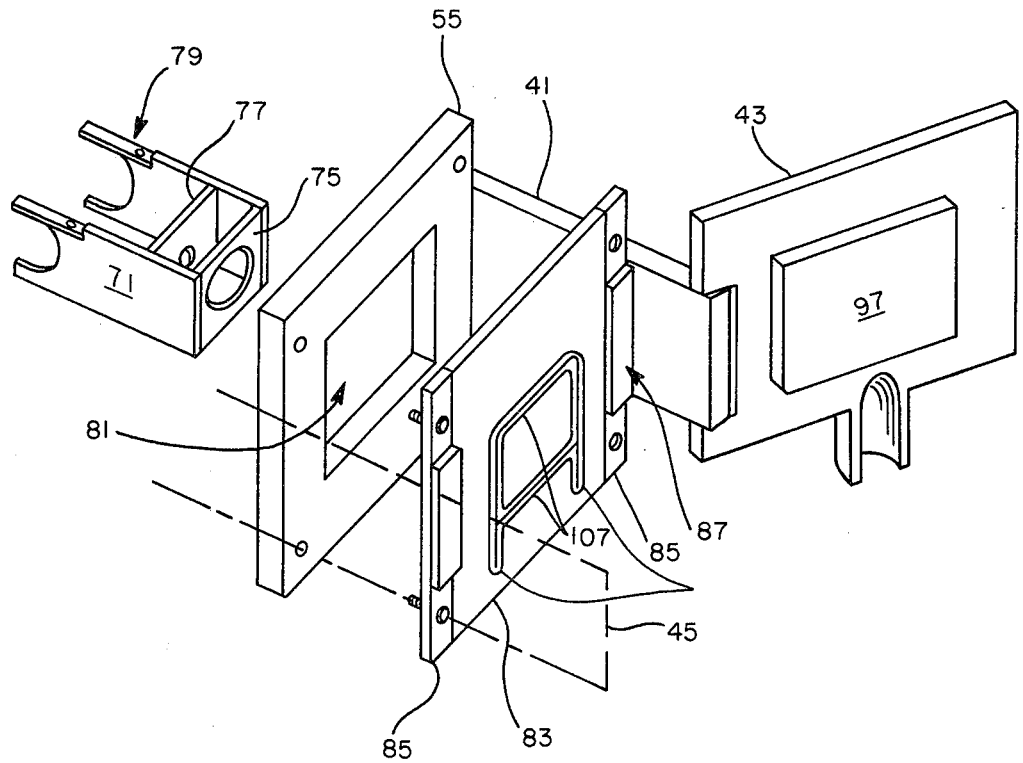
FIG. 4 is an exploded, perspective view of a part of the structure of FIG. 3.
Figure 3:
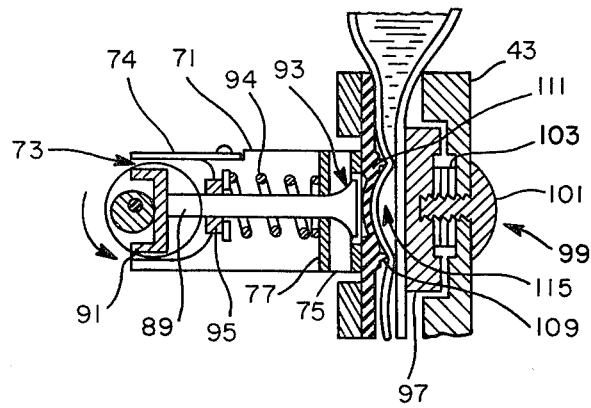
FIG. 3 is a detailed cross-sectional view of the portion of the structure of FIG. 1 delineated by the dotted circle 3—3.

Considering also FIGS. 3-5 in combination with FIG. 2, the details of the fluid pumping and control scheme according to the present invention may now be described. Cams 61 are identical in shape and phase or orientation, such that as they rotate they drive in unison a pair of rocker arms 71, each of which is provided with an arcuate recess at one end to form that end into a yoke 73 for engaging one of the cams 61, as best seen in FIGS. 3 and 4. Rocker arms 71 are interconnected at their other ends by a transversely extending apertured rocker plate 75, and are further interconnected by a transverse bulkhead 77, to form a relatively rigid rocker assembly 79.

As shown in FIG. 4, front plate 55 has a central aperture 81 to receive rocker assembly 79 therewithin, and has a relatively thin block 83 of a compliant and resilient material such as silicone rubber joined to its face, for example by being bonded thereto with a suitable adhesive. Similarly, the face of rocker plate 75 is bonded to block 83 coaxially within aperture 81. Flanking block 83 are a pair of bearing strips 85 which may be joined to front plate 55 with screws, for example. As shown in FIG. 4, strips 85 are each provided with raised bearing portions 87.

As best illustrated by FIG. 3, a pump plunger 89 extends coaxially through rocker assembly 79, and is provided with a cam follower 91 in contact with the surface of small eccentric cam 63 at one end. The other end of plunger 89 is provided with an enlarged plunger head 93. A pump spring 94 around plunger 89 is compressed between bulkhead 77 and an adjustable spring stop 95 (for example, a nut and washer or a collar with setscrews), which is variably positionable along plunger 89 to adjust the compressive force of spring 94. Spring 94 serves both to maintain follower 91 in contact with cam 63, and to urge rocker assembly 79 toward block 83.

As shown in FIGS. 3 and 4, a planar, rigid pressure plate 97 is mounted within a shallow recess on the inner face of door 43 by means of a central pivoting mount 99. Mount 99 presses plate 97 toward block 83 when the door is closed, and permits the pressure plate to pivotally adjust its position slightly on contact with block 83 to ensure equal pressure in all regions of contact. In the prototypical version illustrated in FIGS. 3 and 4, mount 99 is simply made of a screw 101 linking door 43 and pressure plate 97, with a plurality of washers 103 permitting slight angular deviation between the two. However, it will be realized that a production version of mount 99 might employ simpler means for accomplishing the same ends, such as a molded ball-and-socket joint.

Figure 5:
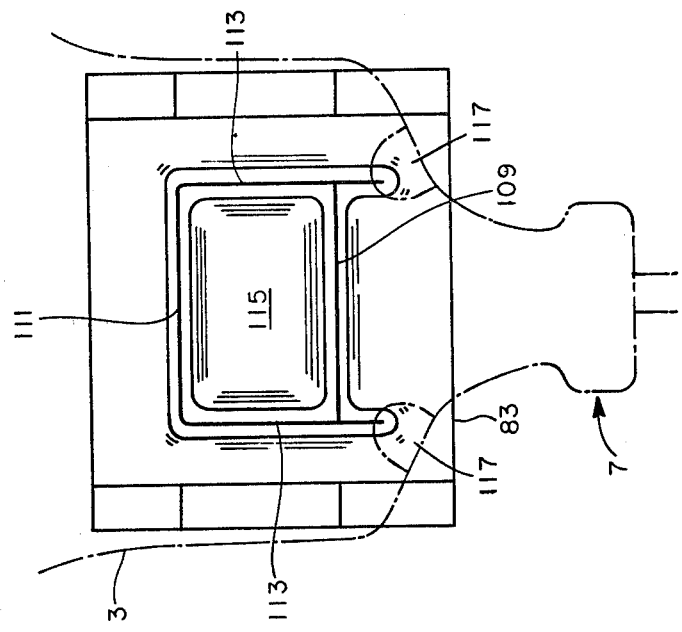
FIG. 5 is a view showing the means of occlusively defining a flow channel and pumping region in a flexible bag according to the present invention.

The outer face of rubber block 83 is provided with a raised plateau as shown in FIGS. 4 and 5, formed by a pair of spaced, parallel vertically extending legs 105, and a pair of spaced, parallel horizontally extending legs 107. Each of these legs is surmounted by a central protuberant ridge, such that there are a pair of spaced horizontal ridges 109 and 111, and similar vertical ridges 113. Moreover, bearing strips 85 are dimensioned such that raised bearing portions 87 lie essentially in the plane of the plateau formed by legs 105 and 107, causing ridges 109-113 to extend slightly beyond this plane in a direction toward pressure plate 97.

As a result, when a flexible bag 3 is enclosed between rubber block 83 and pressure plate 97 upon closure of door 43, each of ridges 109-113 presses into the bag to create in the immediate vicinity of each ridge, a region from which all fluid has been expelled, such that within this region the bag is fully occluded. The effect is quite clearly illustrated in the cross-sectional drawing of FIG. 3, from which it can be seen that a first region of occlusion has been produced adjacent the outlet port (not shown, but at the bottom of FIG. 3) by ridge 109, effectively isolating the outlet port from the fluid contents of the bag. Similarly, ridge 111 has produced a second region of occlusion which is spaced from the first region, to define therebetween an unoccluded region 115 which is isolated from both the outlet port and the remaining contents of the bag.

As will be evident to those skilled in the art, if some means were provided to alternately remove and replace the occlusions within the above first and second regions of occlusion, unoccluded region 115 would first fill with fluid from the fluid content of the remainder of the bag above it, and then empty its contents into the outlet port below (assuming a gravity-flow system with a slight negative pressure head at the outlet port). In fact, exactly this effect may be achieved by the action of large eccentric cams 61 and rocker assembly 79 on rubber block 83.

As cams 61 rotate, their eccentricity presses yoke 73 upwardly and downwardly. The exact nature of the corresponding movement of yoke 73 depends upon the stiffness or spring constant of a countervailing leaf spring 74 which forms the upper leg of yoke 73. The discussion immediately following is based upon the assumption that spring 74 has been dimensioned to have a very high spring constant indeed, such that it deflects negligibly and behaves exactly as the lower leg of yoke 73. The refinements introduced by the selection of a lower spring rate for spring 74 will be dealt with later.

Accordingly, the upward and downward movements of cams 61 as they rotate will induce equal upward and downward movements of yoke 73, deforming block 83 and alternately withdrawing ridges 109 and 111 from their positions of compressive contact with bag 3. Considered more specifically, the eccentric motion of cams 61 causes the left end of rocker assembly 79 (in FIG. 3) to move up and down, while the right end of this assembly is continuously urged to the right in FIG. 3 and is held in firm compressive contact with block 83 under the influence of spring 94.

The combined effect of these mechanical constraints is to cause rocker assembly 79 to pivot downwardly about an axis which approximately coincides with lower horizontal ridge 109, and alternately, to pivot upwardly about an axis approximately coincident with upper horizontal ridge 111. Each of these pivoting motions about one of the horizontal ridges is accompanied by the simultaneous movement of the other ridge to the left in FIG. 3, away from a position in which the concerned ridge was compressing bag 3 against pressure plate 97 and producing a corresponding region of occlusion.

It is worthwhile noting that rocker assembly 79, operating under the above mechanical constraints, serves as a means to link the movements of ridges 109 and 111 in such a way that the withdrawing of either of these ridges from compressive contact with bag 3 is invariably preceded by the movement of the other ridge into firm compressive contact with bag 3. In fact, as yoke 73 moves up the pressure exerted by spring 94 on ridge 111 actually increases to nearly double that which is produced upon each of ridges 109 and 111 with yoke 73 in its mid-position; the same is true of the pressure on ridge 109 when yoke 73 moves down. Consequently, the arrangement virtually precludes the occurrence of an uncontrolled high flow rate from bag 3, as could happen if both ridges were simultaneously withdrawn.

Thus, within the context of the present invention, horizontal ridges 109 and 111 together with pressure plate 97 form first and second occlusion means, each having a closed position in which a corresponding region of bag 3 is occluded and an open position in which the region is at least partially unoccluded. Similarly, rocker assembly 79 together with the associated electrical and mechanical elements which cause rocker assembly 79 to rock up and down, alternately pressing ridges 109 and 111 into bag 3 and withdrawing them from bag 3, may be described broadly as a pump actuating means to sequentially operate the above first and second occlusion means. Taken together, such occlusion means and pump actuating means fundamentally define a flow-regulating pump capable of controlling the fluid flow from a flexible bag of fluid in a gravity-flow system.

In the embodiment described thus far, bag 3 conveniently serves as a reservoir at the upstream end of a serial fluid flow path extending through the active portion of the pump located below. Bag 3 is also intimately involved in the pump mechanism, since its thin flexible walls near its outlet end actually bound or define a portion of the fluid flow path. However, the invention is not limited to the use of such a convenient, dual-purpose element as bag 3, and could be embodied as well in an arrangement having a rigid reservoir supplying fluid to a region of the flow path bounded by thin, flexible walls enclosed within the same sort of pumping mechanism as is illustrated in FIG. 3.

In either case, the establishment and maintenance of a constant flow rate in such a pump is an object of concern. Fundamentally, flow rate depends upon just two variables: (1) the frequency of filling and emptying the unoccluded pumping region between ridges 109 and 111; (2) the net volume of fluid delivered to the outlet port for each such cycle. The first of these variables has been adequately brought under control in the already described apparatus by the incorporation of variable speed controller 65, which can quite easily be selected to provide a very high order of control and monitoring of motor speed. Consequently, it is to the second of the above variables which we now turn our attention.

FIGS. 3, 4, and 5 show that ridges 109–113 enclose a rectangular surface region on the face of block 83, and that this region when viewed in cross section comprises a shallow depression 115. When upper horizontal ridge 111 has been withdrawn, the unoccluded pumping region between the two ridges will fill with fluid until the consequent swelling of this region of the bag is limited by contact with the surface of depression 115. Consequently, depression 115 effectively serves as a means to define the volumetric capacity of the unoccluded pumping region of bag 3, as clearly shown in FIG. 3. Depression 115 thus completely establishes the volume of fluid which will be delivered to the outlet port if it may be assumed that the unoccluded pumping region is fully evacuated of fluid whenever lower horizontal ridge 109 is withdrawn.

In order to ensure that the unoccluded pumping region is fully evacuated of fluid during each pumping cycle, and to permit operation of the pump irrespective of the pressure head present at the outlet port, the present invention utilizes plunger 89, driven by small eccentric cam 63 to positively express fluid from the unoccluded pumping region. However, the actual quantity of fluid delivered into the outlet at each stroke is yet subject to some uncertainties.

In particular, if lower ridge 109 is withdrawn from occlusive contact with bag 3 at the moment of evacuation of the pumping region, this region is exposed to whatever pressure head is present in the outlet line. If this pressure is slightly negative as it well might be in a gravity-flow system, the pumping region may become substantially fully evacuated, such that the flexible walls of bag 3 in the pumping region are drawn together with a thin film of fluid between them. Such a condition is undesirable, since the resulting capillary forces are sufficient to interfere with the proper filling of the pumping region when ridge 111 is next opened.

Furthermore, the quantity of fluid delivered to the outlet under such conditions is greater than could have been delivered by the action of plunger 89 alone, since there are always small void spaces between region 115 and pressure plate 97, even when plunger 89 is at the full extent of its rightward travel in FIG. 3. Consequently, the maintenance of a constant flow rate irrespective of the outlet pressure head would be impossible if ridge 109 were withdrawn from complete contact with bag 3 and pressure plate 97.

In accordance with the present invention, these problems can be overcome if lower ridge 109 is maintained fully in occlusive contact with bag 3 at the start of the pumping stroke of plunger 89, but under a preselected reduced contact pressure, such that plunger 89 must compress the fluid within the pumping region sufficiently to overcome the occlusion produced by ridge 109. As noted earlier in this application, the description of the apparatus thus far has treated countervailing spring 74 as a rigid member, such that yoke 73 is deflected up and down in equal amounts. In practice, spring 74 is chosen to have a spring constant which is just sufficient to substantially reduce but not eliminate the occlusive pressure along ridge 109 when cams 61 have rotated upwardly in FIG. 3.

Under this circumstance, ridge 109 will be maintained in light occlusive contact with bag 3 over the entire length of ridge 109, but no fluid will flow into the outlet except under the influence of the compressive force of plunger 89, Consequently, the quantity of fluid expressed from the pumping region is determined entirely by the geometry of the pump-bag interface region, including the stroke depth of plunger 89, and is independent of the pressure present in the outlet line over a useful range of pressures.

The correct timing of the stroke of plunger 89 is easily established by the rotational positioning of the cams on shaft 59. As shown by the circular arrow in FIG. 3, the rotation of shaft 59 is counterclockwise. Further, it will be noted that for counterclockwise rotation of cams 61 and 63, the eccentricity of small cam 63 lags the eccentricity of cams 61 by about 90 degrees. Consequently, when cams 61 have rotated to a position in which their eccentricity has driven yoke 73 up, thus reducing the occlusive pressure along ridge 109, cam 63 is in a position such that plunger 89 is driven fully to the right in FIG. 3, and plunger head 93 has fully collapsed the unoccluded pumping region, expressing its fluid contents into the outlet port.

Thus plunger 89 may be viewed within the context of the present invention as a pumping means having a first state in which the pumping region between ridges 109 and 111 is uncompressed, and a second state in which this region is compressed. Similarly, the electrical and mechanical elements associated with the movement of plunger 89 in concert with the movement of ridges 109 and 111 to execute the complete pumping cycle outlined above may be viewed broadly as pump actuating means to sequentially operate plunger 89 and ridges 109 and 111 in the described cycle.

Turning now to FIG. 5, the nature of the interface between bag 3 and pump 1 will be more closely examined. FIG. 5 illustrates rubber block 83 flanked on either side by bearing strips 85, with the phantom outline 115 of a flexible bag 3 in position over block 83 as it would be prior to closure of door 43. Bag 3 will in general have been formed of a pair of thin plastic sheets welded, or "heat-sealed" together along a periphery which has the shape illustrated by phantom outline 115 in FIG. 5.

Although it might seem practical to dimension ridges 109 and 111 such that they extend fully to the edges of bag 3, there are reasons why this is not feasible. The common processes of welding the peripheral seam of such plastic bags often create a rather thick, somewhat roughened and distorted edge, making occlusion of the region near such an edge difficult or impossible. Consequently, a certain amount of fluid would continuously leak past ridges 109 and 111, making the establishment of a desired flow rate somewhat problematical.

A second source of inaccuracy would arise from the difficulty of maintaining a consistent width, and hence volume, of the unoccluded pumping region, since that width would be determined only by the width of the bag 3 in the space between ridges 109 and 111. The processes used to form such disposable bags do not generally favor the maintenance of extreme dimensional accuracy.

Consequently, vertically extending ridges 113 have been provided intersecting ridges 109 and 111 and defining a unitary flow channel through which all fluid effluent from the bag must pass. Ridges 113 function together with pressure plate 97 similarly to ridges 109 and 111, with the exception that they occlude bag 3 continuously, and are not disturbed by the movements of rocker assembly 79 or plunger 89.

In order to extend the flow channel created by ridges 113 fully to the edges of bag 3 on either side of the outlet at juncture 7, a pair of heat-sealed, semicircular regions 117 are formed, serving as a "bridge" to extend the occluded regions created by ridges 113 fully to the edge of the bag. The technique of forming such heat-sealed regions is the subject matter of copending U.S. patent application Ser. No. 253,083, filed Apr. 13, 1981, entitled "Plastic Bag Configuration For Sealing to Edge Welded Seam", commonly assigned with the present application.

Figure 6:
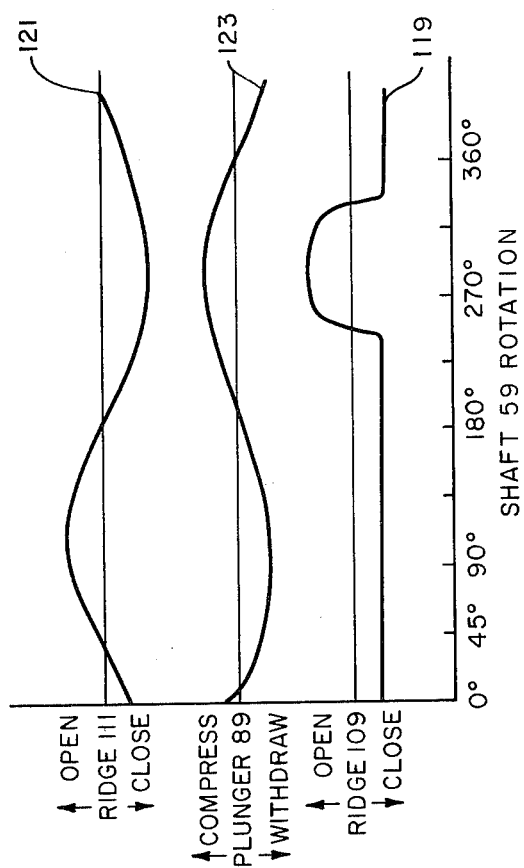
FIG. 6 is a timing diagram showing details of the pumping action accomplished by the present invention.

FIG. 6 illustrates in a graphical way the movements of ridges 109 and 111, and plunger 89 which together produce the pumping action of the present invention. The abscissa in FIG. 6 is a scale of rotation of shaft 59, and hence cams 61 and 63, with 0 degrees being somewhat arbitrarily selected as the time when ridge 109 has "closed", or fully occluded the bag. In FIG. 6, characteristic 119 represents the movement of ridge 109, and characteristic 121, the movement of ridge 111, while characteristic 123 represents the movement of plunger 89.

As shown, the portions of the cycle during which either ridge 109 or 111 is open are shorter than the portions when they are closed. Moreover, the open portions of the cycle for the two ridges are 180 degrees apart, providing sufficient overlap between the regions of full occlusion so that at no position of the rotational cycle are both ridges 109 and 111 unoccluded. Finally, as noted earlier, the motion of plunger 89 is timed by the relative phase of cams 61 and 63 to coincide with the movement of ridge 109 to the open position.

Several features of these characteristics are worth noting by way of understanding the operation of the embodiments of this invention. Characteristics 121 and 123 are sinusoidal, and hence, rather gradual in the way in which they produce the described pumping effects. Consequently, characteristic 121 has been labeled with the ordinates "open" and "closed" indicated only by arrows showing the directions for opening and closure of the occlusion created by ridge 111.

The actual level which must be reached by characteristic 121 before fluid can flow into the pumping region is a matter of design in view of the flow rates involved and other, geometric considerations. The same is true of characteristic 123.

Finally, characteristic 119 clearly shows that ridge 109 only opens, permitting fluid flow to the outlet, when the pressure created by plunger 89 has reached some positive value, which may similarly be selected by appropriately choosing the spring constant of spring 74 in view of the spring rate of main spring 94 and the geometry of the associated parts.

Although the invention of this application has been described with some particularity in reference to a preferred embodiment which comprises the best mode known to the inventor for carrying out his invention, those skilled in the art will realize that many changes could be made and many alternative embodiments thus derived without departing from the scope of the invention. Especially it will be realized that the disclosed embodiment is basically a prototype, and that while this prototype represents the best mode known to the inventors for carrying out their invention at the present time, many changes to the disclosed structure would likely be necessary for the sake of economy, manufacturability, and other considerations of a basically commercial nature. Consequently, the scope of the invention is to be interpreted only from the following claims.

What is claimed is:

1. A flow-regulating pump for controlling the flow rate of fluid along a serial fluid flow path extending through said pump from a reservoir located above said pump at the upstream end of said flow path, especially for use in an apparatus for administering a fluid internally to the human body for the purpose of enteric feeding, said fluid flow path being bounded over a certain region therealong by generally thin flexible walls, said flow-regulating pump comprising:
   pump frame means to engage and support said reservoir above said region bounded by flexible walls;
   first occlusion means to compress said flexible walls together to occlude said flow path within a first region extending transversely thereacross, said occlusion means being selectively operable between a closed position in which said first region is fully occluded and an open position in which said first region is at least partially unoccluded;
   second occlusion means to compress said flexible walls together to occlude said flow path within a second region extending transversely thereacross, said second region being adjacent to said first region but spaced therefrom in a direction toward said reservoir to define between said first and second regions an unoccluded pumping region, said second occlusion means being selectively operable between a closed position in which said second region is fully occluded and an open position in which said second region is at least partially unoccluded; and,
   pump actuating means to sequentially operate said first and second occlusion means in the following cycle: occlude first region, open second region, occlude second region, open first region, said pump actuating means including pumping means to compress said pumping region to express any fluid contained therein, and;
   means to produce a first higher pressure within said second region when closed, and means to produce a second lower pressure within said first region following the closure of said second region and prior to the opening of said first region, wherein said pumping means compresses said pumping region sufficiently to overcome said second lower pressure and open said first region.

2. The flow-regulating pump of claim 1 wherein said pump-actuating means comprises:
   main spring means to produce said first higher pressure within said first and second regions when closed; and,
   countervailing spring means to oppose said main spring means to produce said second lower pressure within said first region prior to the opening of said first region.

3. A flow-regulating pump for controlling the flow rate of fluid along a serial fluid flow path extending through said pump from a reservoir located above said pump at the upstream end of said flow path, especially for use in an apparatus for administering a fluid internally to the human body for the purpose of enteric feeding, said fluid flow path being bounded over a certain region therealong by generally thin flexible walls, said flow-regulating pump comprising;
   pump frame means to engage and support said reservoir above said region bounded by flexible walls;
   first occlusion means to compress said flexible walls together to occlude said flow path within a first region extending transversely thereacross, said occlusion means being selectively operable between a closed position in which said first region is fully occluded and an open position in which said first region is at least partially unoccluded;
   second occlusion means to compress said flexible walls together to occlude said flow path within a second region extending transversely thereacross, said second region being adjacent to said first region but spaced therefrom in a direction toward said reservoir to define between said first and second regions an unoccluded pumping region, said second occlusion means being selectively operable between a closed position in which said second region is fully occluded and an open position in which said second region is at least partially unoccluded;
   one of said occlusion means including first and second pressure-sealing members so mounted on said pump frame means as to be positionable in facing opposition to one another, said flexible walls being receivable between said pressure-sealing members when said reservoir is supported upon said frame, said one occlusion means further including a protuberant ridge on one of said pressure-sealing members positioned and oriented on a surface of said member facing the other of said members to compressively occlude said flexible walls between said ridge and the other of said pressure sealing members when said members are brought together; and,
   pump actuating means to sequentially operate said first and second occlusion means in the following cycle: occlude first region, open second region, occlude second region, open first region, whereby fluid flows from the reservoir into the pumping region, the pumping region is then isolated from the remainder of the fluid flow path, and the fluid trapped in the pumping region is released to flow along the fluid flow path.

4. The flow-regulating pump of claim 3 wherein one of said pressure-sealing members comprises a door pivotally mounted on said frame means and having an open position in which said pressure-sealing members are separated to permit positioning of said flexible walls therebetween, and a closed position in which said pressure-sealing members are brought together with said flexible walls sandwiched therebetween.

5. A flow-regulating pump for controlling the flow rate of fluid along a serial fluid flow path extending through said pump from a reservoir located above said pump at the upstream end of said flow path, especially for use in an apparatus for administering a fluid internally to the human body for the purpose of enteric feeding, said fluid flow path being bounded over a certain region therealong by generally thin flexible walls, said flow-regulating pump comprising:

pump frame means to engage and support said reservoir above said region bounded by flexible walls;

first occlusion means to compress said flexible walls together to occlude said flow path within a first region extending transversely thereacross, said occlusion means being selectively operable between a closed position in which said first region is fully occluded and an open position in which said first region is at least partially unoccluded;

second occlusion means to compress said flexible walls together to occlude said flow path within a second region extending transversely thereacross, said second region being adjacent to said first region but spaced therefrom in a direction toward said reservoir to define between said first and second regions an unoccluded pumping region, said second occlusion means being selectively operable between a closed position in which said second region is fully occluded and an open position in which said second region is at least partially unoccluded; and, pump actuating means to sequentially operate said first and second occlusion means in the following cycle: occlude first region, open second region, occlude second region, open first region, said pump actuating means including linking means having a rocker member mechanically interconnecting said first and second occlusion means to link the movements of said first and second occlusion means to cause one of said occlusion means to be in said closed position prior to the other of said occlusion means being opened.

6. The flow-regulating pump of claim 5 wherein said pump actuating means includes electromagnetic driver means to drive said rocker member to operate said occlusion means sequentially through said cycle.

7. The flow-regulating pump of claim 6 wherein said electromagnetic driver means comprises an electric rotary motor, an eccentric cam driven by said motor, and yoke means to couple the eccentric motion of said cam to said rocker member.

8. A flow-regulating pump for controlling the flow rate of fluid along a serial fluid flow path extending through said pump from a reservoir located above said pump at the upstream end of said flow path, especially for use in an apparatus for administering a fluid internally to the human body for the purpose of enteric feeding, said fluid flow path being bounded over a certain region therealong by generally thin flexible walls in the form of a bag formed of fluid-impervious material extending from the reservoir to an outlet port thereof, said flow-regulating pump comprising:

pump frame means to engage and support said reservoir above said region bounded by flexible walls;

bag-support means to suspend said bag with said outlet port generally lower than the fluid contents of said bag;

first occlusion means to compress said flexible walls together to occlude said flow path within a region extending transversely thereacross, said occlusion means being selectively operable between a closed position in which said first region is fully occluded and an open position in which said first region is at least partially unoccluded; said first occlusion means occluding said bag adjacent said outlet port and isolating said outlet port from the fluid contents of said bag;

second occlusion means to compress said flexible walls together to occlude said flow path within a second region extending transversely thereacross, said second region being adjacent to said first region but spaced therefrom in a direction toward said reservoir to define between said first and second regions an unoccluded pumping region, said second occlusion means being selectively operable between a closed position in which said second region is fully occluded and an open position in which said second region is at least partially unoccluded; said second occlusion means occluding said bag and isolating said pumping region from the fluid contents of said bag; and pump actuating means to sequentially operate said first and second occlusion means in the following cycle: occlude first region, open second region, occlude second region, open first region.

9. The flow-regulating pump of claim 8 further comprising flow-channel-defining means to define a unitary flow channel extending from said outlet port toward the interior of said bag, through which fluid effluent from said bag must pass.

10. The flow-regulating pump of claim 9 wherein said flow-channel-defining means comprises a third occlusion means, extending from an edge of said bag adjacent to and on one side of said outlet port, toward the interior of said bag, to occlude said bag to define one edge of said flow channel.

11. The flow-regulating pump of claim 10 wherein said flow-channel-defining means further comprises a fourth occlusion means, extending from an edge of said bag adjacent to and on the other side of said outlet port from said third occlusion means, toward the interior of said bag, to occlude said bag to define the other edge of said flow channel.

12. The flow-regulating pump of claim 11 wherein said first, second, third, and fourth occlusion means are arrayed in the form of a generally planar polygon, and wherein said unoccluded pumping region comprises the region within said polygon.

13. The flow-regulating pump of claim 12 wherein said arrayed occlusion means comprise a block of a resilient and compliant material, and a plurality of protuberant ridges formed on one face of said block in a polygonal array.

14. The flow regulating pump of claim 13 wherein said array of ridges encloses a shallow recess on said one face of said block.

15. The flow-regulating pump of claim 9 wherein said first and second occlusion means extend generally transversely fully across said flow channel, thereby defining said unoccluded pumping region within said flow channel.

16. A flow-regulating pump for controlling the flow rate of fluid along a serial fluid flow path extending through said pump from a reservoir at the upsteam end of said flow path, especially for use in an appartus for administering a fluid internally to the human body for the purpose of enteric feeding, said fluid flow path being bounded over a certain region therealong by generally thin flexible walls, said flow-regulating pump comprising:

first occlusion means to compress said flexible walls together to occlude said flow path within a first region;

second occlusion means to compress said flexible walls together to occlude said flow path within a second region, said second region being adjacent to said first region but spaced therefrom in a direction toward said reservoir to define between said first and second regions an unoccluded pumping region;

said first region being at least partially unoccluded and open to permit fluid flow past said first region only when said second region is fully occluded and closed, said second region being at least partially unoccluded and open only when said first region is fully occluded and closed;

pumping means for compressing said pumping region after said second region is closed to force fluid in said pumping region past said first region along the fluid flow path;

means for producing a first higher pressure within said second region when closed; and means for producing a second lower pressure within said first region after said second region is closed and before said first region is opened, wherein the pressure exerted by said pumping means is sufficient to overcome said second lower pressure but not said first higher pressure such that fluid is forced past said first region to open said first region.

17. The flow regulating pump according to claim 16 in which said first region is partially occluded by said first occlusion means when said first region is open.

18. The flow-regulating pump of claim 16 wherein said pumping means comprises:

main spring means to produce said first higher pressure within said first and second regions when closed; and, countervailing spring means to oppose said main spring means to produce said second lower pressure within said first region prior to the opening of said first region.

19. The flow-regulating pump according to claim 16 further including volume-defining means surrounding said pumping region to define the volumetric capacity thereof.

20. The flow-regulating pump according to claim 16 wherein one of said occlusion means comprises first and second pressure-sealing members in facing opposition to one another, and wherein said flexible walls are receivable between said pressure-sealing members.

21. The flow-regulating pump of claim 20 wherein one of said pressure-sealing members comprises a generally compliant material.

22. The flow-regulating pump of claim 20 wherein one of said pressure-sealing members comprises a pivoted generally incompliant plate.

23. The flow-regulating pump of claim 16 including linking means to link the movements of said first and second occlusion means to cause one of said occlusion means to be in said closed position prior to the other of said occlusion means being opened.

* * * * *